United States Patent [19]

Takaya et al.

[11] 4,399,277

[45] Aug. 16, 1983

[54] 7-AMINO-3-PHOSPHONOCEPHALOSPORANIC ACID COMPOUNDS

[75] Inventors: Takao Takaya, Kawanishi; Toshiyuki Chiba, Osaka, both of Japan

[73] Assignee: Fujisawa Pharmaceutical Co., Ltd., Osaka, Japan

[21] Appl. No.: 245,718

[22] Filed: Mar. 20, 1981

Related U.S. Application Data

[62] Division of Ser. No. 119,437, Feb. 7, 1980, Pat. No. 4,291,031.

[30] Foreign Application Priority Data

Feb. 19, 1979 [GB] United Kingdom ................. 7905790

[51] Int. Cl.³ .......................................... C07D 501/18
[52] U.S. Cl. .................................... 544/016; 424/246; 544/17; 544/22
[58] Field of Search ........................ 544/16, 17, 26, 27

[56] References Cited

U.S. PATENT DOCUMENTS

| | | | |
|---|---|---|---|
| 3,278,531 | 10/1966 | Cox et al. | 260/243 |
| 3,769,277 | 10/1973 | Long et al. | 544/16 |
| 3,998,821 | 12/1976 | Weir | 544/16 |
| 4,043,991 | 8/1977 | Hamma et al. | 544/16 |
| 4,066,641 | 1/1978 | Hamashima et al. | 544/16 |
| 4,150,223 | 4/1979 | Christensen et al. | 544/16 |
| 4,166,155 | 8/1979 | Takaya et al. | 424/246 |
| 4,291,031 | 9/1981 | Takaya et al. | 544/21 |

Primary Examiner—Nicholas S. Rizzo
Attorney, Agent, or Firm—Oblon, Fisher, Spivak, McClelland & Maier

[57] ABSTRACT

A compound of the formula:

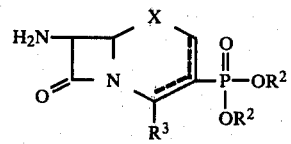

wherein $R^2$ is hydrogen or lower alkyl, $R^3$ is carboxy or a protected carboxy group, X is —S— or

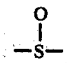

and the dotted line bridging the 2- to 4-positions of the formula indicates that the compound may be the 2- or 3-cephem derivative, and pharmaceutically acceptable salts thereof.

5 Claims, No Drawings

7-AMINO-3-PHOSPHONOCEPHALOSPORANIC ACID COMPOUNDS

This is a divisional, of application Ser. No. 119,437, filed Feb. 7, 1980 now U.S. Pat. No. 4,291,031.

The present invention relates to novel 3-phosphonocephalosporanic acid derivatives and pharmaceutically acceptable salts thereof. More particularly, it relates to novel 3-phosphonocephalosporanic acid derivatives and pharmaceutically acceptable salts thereof, which have anti-microbial activities, to processes for the preparation thereof, to pharmaceutical composition comprising the same, and to a method of using the same therapeutically for the treatment of infectious diseases in human being and animals.

Accordingly, one object of the present invention is to provide novel 3-phosphonocephalosporanic acid derivatives and pharmaceutically acceptable salts thereof, which are highly active against a number of pathogenic microorganisms.

Another object of the present invention is to provide processes for the preparation of novel 3-phosphonocephalosporanic acid derivatives and salts thereof.

A further object of the present invention is to provide pharmaceutical composition comprising, as an active ingredient, said 3-phosphonocephalosporanic acid derivatives and pharmaceutically acceptable salts thereof.

Still further object of the present invention is to provide a method for the treatment of infectious diseases by pathogenic microorganisms in human being and animals.

The object 3-phosphonocephalosporanic acid derivatives are novel and comprise a new and unique 3-phosphonocephem ring in the chemical structure, which have not been expected to any persons skilled in the art, and can be represented by the following general formula:

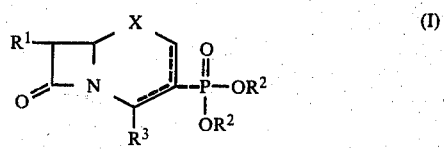
(I)

wherein
R$^1$ is amino or a protected amino group,
R$^2$ is hydrogen or lower alkyl,
R$^3$ is carboxy or a protected carboxy group,
X is -S- or

and the dotted line bridging the 2 to 4-positions of the formula indicates that the compound may be 2 or 3-cephem derivative, and pharmaceutically acceptable salts thereof.

In the object compound (I) and the corresponding starting compound (II) of Process 1 mentioned below, it is to be understood that there may be one or more stereoisomeric pair(s) such as optical and/or geometrical isomers due to asymmetric carbon atom(s) and double bond(s) in those molecules, and these isomers are also included within the scope of the present invention.

Suitable pharmaceutically acceptable salts of the object compounds (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), and an ammonium salt etc.; an organic salt, for example, an organic amine salt (e.g., trimethylamine, salt, triethylamine salt, pyridine salt, picoline salt, dicyclohexylamine salt, N,N'-dibenzylethylenediamine salt, N-methylglucamine salt, diethanolamine salt, triethanolamine salt, tris-(hydroxymethylamino)methane salt, etc.) etc.; an organic carboxylic or sulfonic acid addition salt (e.g., formate, acetate, maleate, tartrate, methanesulfonate, benzenesulfonate, toluenesulfonate, etc.); an inorganic acid addition salt (e.g., hydrochloride, hydrobromide, sulfate, phosphate, etc.); a salt with a basic or acidic amino acid (e.g., arginine, aspartic acid, glutamic acid, etc.), and the like.

According to the present invention, the object compound (I) and the pharmaceutically acceptable salts thereof can be prepared by the processes as illustrated by the following reaction schemes.

(1) Process 1:

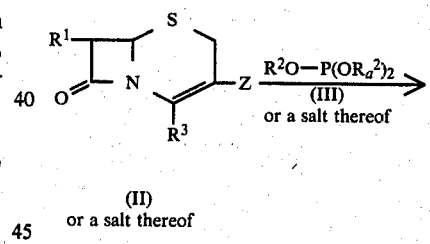

(II)
or a salt thereof

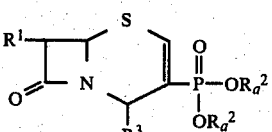

(I-a)
or a salt thereof (2) Process 2:

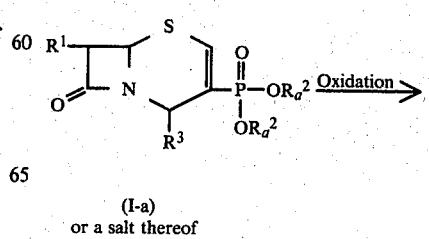

(I-a)
or a salt thereof

-continued

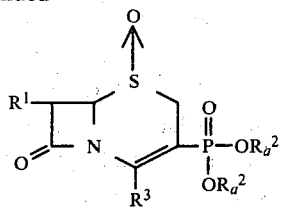

(I-b)
or a salt thereof (3) Process 3:

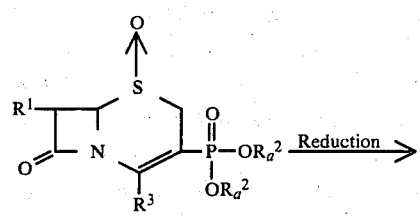

(I-b)
or a salt thereof

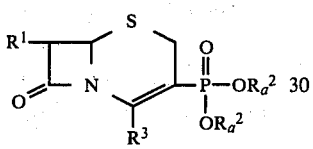

(I-c)
or a salt thereof (4) Process 4:

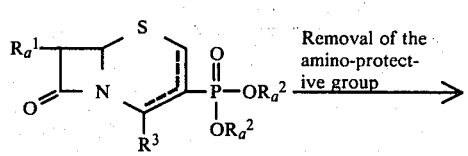

(I-d)
or a salt thereof

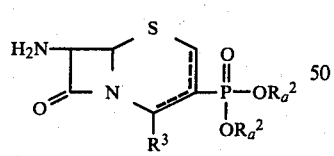

(I-e)
or a salt thereof (5) Process 5:

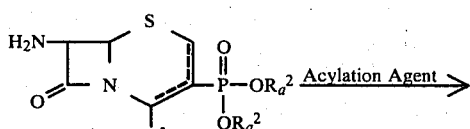

(I-e)
or a salt thereof

-continued

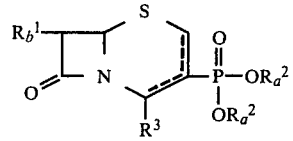

(I-f)
or a salt thereof (6) Process 6:

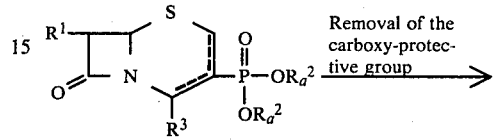

(I-g)
or a salt thereof

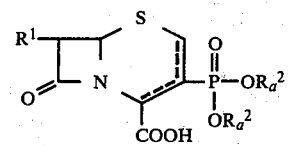

(I-h)
or a salt thereof (7) Process 7:

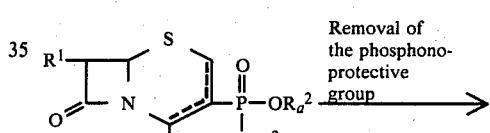

(I-i)
or a salt thereof

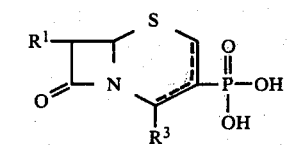

(I-j)
or a salt thereof wherein
$R^1$, $R^2$ and $R^3$ are each as defined above,
$R_a^1$ is a protected amino group,
$R_b^1$ is acylamino,
$R_a^2$ is lower alkyl,
$R_a^3$ is protected carboxy group,
Z is an acid residue, and the dotted line indicates as defined above.

Some of the starting compound (II) in Process 1 are novel and can be, for example, prepared from 3-hydroxycephalosporanic acid derivatives (II-a) by the method in the following reaction schemes.

(A) Preparation A:

-continued

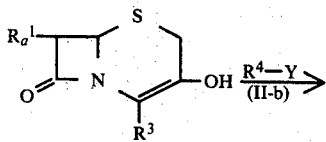

(II-a)
or a salt thereof

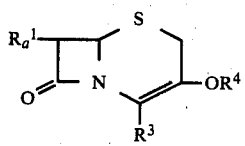

(II-c)
or a salt thereof (B) Preparation B:

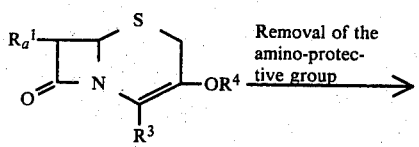

(II-c)
or a salt thereof

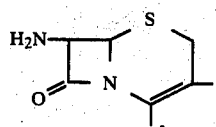

(II-d)
or a salt thereof (C) Preparation C:

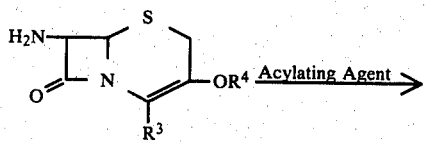

(II-d)
or a salt thereof

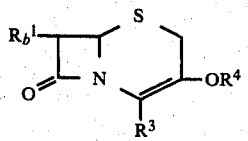

(II-e)
or a salt thereof wherein
$R_a^1$, $R_b^1$ and $R^3$ are each as defined above,
$R^4$ is lower alkanesulfonyl or arenesulfonyl and Y is halogen.

The other starting compound (III) in Process 1 are known compound and can be prepared from phosphorus trihalide and alkali metal alkoxide or in a conventional manner.

In the above and subsequent description of the present specification, suitable examples and illustration of the various definitions to be included within the scope thereof are explained in detail as follows.

The term "lower" in the present specification is intended to mean a group having 1 to 6 carbon atom(s) and the term "higher" is intended to mean a group having 7 to 18 carbon atoms, unless otherwise provided.

Suitable "a protected amino group" may include an amino group substituted with a suitable protective group which is conventionally used in cephalosporin and penicillin compounds as a protective group of the amino group at their 7th or 6th position, and suitable "a protected amino group" may include acylamino, phenyl(lower)alkylamino (e.g. benzylamino, tritylamino, etc.), and the like.

Suitable "acyl moiety" in the term "acylamino" may include aliphatic acyl group and acyl group containing an aromatic ring, which is referred to as aromatic acyl, or heterocyclic ring, which is referred to as heterocyclic acyl.

Suitable example of said acyl may be illustrated as follows:

Aliphatic acyl such as lower or higher alkanoyl (e.g. formyl, acetyl, succinyl, hexanoyl, heptanoyl, stearoyl, etc.);
lower or higher alkoxycarbonyl (e.g. methoxycarbonyl, ethoxycarbonyl, t-butoxycarbonyl, t-pentyloxycarbonyl, heptyloxycarbonyl, etc.);
lower or higher alkanesulfonyl (e.g. methanesulfonyl, ethanesulfonyl, etc.); or the like;
Aromatic acyl such as
aroyl (e.g. benzoyl, toluoyl, naphthoyl, etc.);
ar(lower)alkanoyl such as phenyl(lower)alkanoyl (e.g. phenylacetyl, phenylpropionyl, etc.);
aryloxycarbonyl (e.g. phenoxycarbonyl, naphthyloxycarbonyl, etc.);
aryloxy(lower)alkanoyl such as phenoxy(lower)alkanoyl (e.g. phenoxyacetyl, phenoxypropionyl, etc.);
arylglyoxyloyl (e.g. phenylglyoxyloyl, naphthylglyoxyloyl, etc.);
arenesulfonyl (e.g. benzenesulfonyl, p-toluenesulfonyl, etc.); or the like;
Heterocyclic acyl such as
heterocycliccarbonyl (e.g. thenoyl, furoyl, nicotinoyl, etc.);
heterocyclic(lower)alkanoyl  (e.g. thienylacetyl, thiazolylacetyl, tetrazolylacetyl, etc.);
heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like. And, especially preferable heterocyclic group may be heterocyclic group such as
unsaturated 3 to 8-membered (more preferably 5 or 6-membered)heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.) etc.;

saturated 3 to 8-membered (more preferably 5 or 6-membered)heteromonocyclic group containing 1 to 4 nitrogen atom(s), for example, pyrrolidinyl, imidazolidinyl, piperidino, piperazinyl, etc.:

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, etc.,;

unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered (more preferably 5 or 6-membered) heteromonocyclic group containing an oxygen atom, for example, furyl, etc.;

unsaturated 3 to 8-membered (more preferably 5 or 6-membered)-heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

The acyl moiety thus defined may optionally be substituted by one to ten, same or different, suitable substituent(s) such as:

lower alkyl (e.g. methyl, ethyl, etc.); lower alkoxy (e.g. methoxy, ethoxy, propoxy, etc.); lower alkylthio (e.g. methylthio, ethylthio, etc.); lower alkylamino (e.g. methylamino, etc.); cyclo-(lower)alkyl (e.g. cyclopentyl, cyclohexyl, etc.); cyclo(lower)alkenyl (e.g. cyclohexenyl, cyclohexadienyl, etc.); hydroxy; halogen (e.g. chloro, bromo, etc.); amino; protected amino as aforementioned; cyano; nitro; carboxy; protected carboxy as mentioned below; sulfo, sulfamoyl; imino; oxo; amino(lower)alkyl (e.g. aminomethyl, aminoethyl, etc.); a group of the formula: $=N-OR^5$ wherein $R^5$ is hydrogen, lower alkyl as aforementioned, lower alkenyl (e.g. vinyl, allyl, 2-butenyl, etc.), lower alkynyl (e.g. ethynyl, 2-propynyl, etc.), ar(lower)alkyl such as phenyl(lower)alkyl (e.g. benzyl, phenethyl, etc.), lower alkylthio(lower)alkyl (e.g. methylthiomethyl, methylthioethyl, etc.), carboxy(lower)alkyl (e.g. carboxymethyl, carboxyethyl, etc.) or lower alkyl (e.g. methyl ethyl, etc.) substituted by a protected carboxy as mentioned below.

In this connection, when the acyl moiety has a group of the formula: $=N-OR^5$, wherein $R^5$ is as defined above, as substituent(s), there are geometrical isomers (syn and anti isomers) due to the presence of double bond. And, for example, the syn isomer means one geometrical isomer having the group of the formula:

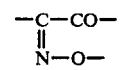

and the corresponding anti isomer means the other geometrical isomer having the group of the formula:

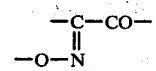

Preferred examples of "a protected amino group" for $R^1$ is acylamino, and more preferably phenyl(lower)alkanoylamino (e.g. 2-phenylacetamido, 3-phenylpropionamido, etc.);

lower alkanoylamino (e.g. formamido, acetamido, etc.);

lower alkanoylamino substituted by a hydroxy and a phenyl (e.g. 2-hydroxy-2-phenylacetamido, 2-hydroxy-3-phenylpropionamido, etc.);

lower alkanoylamino substituted by a phenyl(lower)alkoxycarbonyl and a phenyl (e.g. 2-benzyloxycarbonyl-2-phenylacetamido, 2-benzyloxycarbonyl-3-phenylpropionamido, etc.);

lower alkanoylamino substituted by a lower alkoxyimino and a furyl and the most preferably 2-lower alkoxyimino-2-(2-furyl)acetamido [e.g. 2-methoxyimino-2-(2-furyl)acetamido, 2-ethoxyimino-2-(2-furyl)acetamido, 2-propoxyimino-2-(2-furyl)-acetamido, 2-isopropoxyimino-2-(2-furyl)acetamido, 2-butoxyimino-2-(2-furyl)acetamido, 2-phenyloxyimino-2-(2-furyl)acetamido, 2-hexyloxyimino-2-(2-furyl)acetamido, etc.];

lower alkanoylamino substituted by a lower alkoxyimino and an aminothiazolyl and the most preferably 2-lower alkoxyimino-2-(2-aminothiazol-4-yl)acetamido [e.g. 2-methoxyimino-2-(2-aminothiazol-4-yl)acetamido, 2-ethoxyimino-2-(2-aminothiazol-4-yl)acetamido, 2-propoxyimino-2-(2-aminothiazol-4-yl)-acetamido, 2-isopropoxyimino-2-(2-aminothiazol-4-yl)acetamido, 2-butoxyimino-2-(2-aminothiazol-4-yl)-acetamido, 2-pentyloxyimino-2-(2-aminothiazol-4-yl)-acetamido, 2-hexyloxyimino-2-(2-aminothiazol-4-yl)-acetamido, etc.];

lower alkanoylamino substituted by a lower alkoxyimino and a lower alkanoylaminothiazolyl and the most preferably 2-lower alkoxyimino-2-(2-lower alkanoylaminothiazol-4-yl)acetamido [e.g. 2-methoxyimino-2-(2-formamidothiazol-4-yl)acetamido, 2-ethoxyimino-2-(2-formamidothiazol-4-yl)acetamido, 2-propoxyimino-2-(2-formamidothiazol-4-yl)acetamido, 2-isopropoxyimino-2-(2-formamidothiazol-4-yl)-acetamido, 2-butoxyimino-2-(2-formamidothiazol-4-yl)-acetamido, 2-pentyloxyimino-2-(2-formamidothiazol-4- yl)acetamido, 2-hexyloxyimino-2-(2-formamidothiazol-4-yl)acetamido, etc.]; and the like.

Suitable "lower alkyl" may include methyl, ethyl, propyl, isopropyl, butyl, isobutyl, tert-butyl, pentyl, neopentyl, tert-pentyl, hexyl and the like, and preferred one is $C_1$–$C_3$alkyl and most preferred one is ethyl.

Suitable "a protected carboxy group" may include a carboxy group substituted with a suitable protective group which is conventionally used in cephalosporin and penicillin compounds as the protective group of the carboxy group at their 4th or 3rd position, for example, an esterified carboxy group. And suitable examples of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.);
lower cycloalkyl(lower)alkyl ester (e.g. 1-cyclopropylethyl ester, etc.);
lower alkenyl ester (e.g., vinyl ester, allyl ester, etc.);
lower alkynyl ester (e.g., ethynyl ester, propynyl ester, etc.);
lower alkoxyalkyl ester (e.g., methoxymethyl ester, ethoxymethyl ester, isopropoxymethyl ester, 1-methoxyethyl ester, 1-ethoxyethyl ester, etc.);
lower alkylthioalkyl ester (e.g., methylthiomethyl ester, ethylthiomethyl ester, ethylthioethyl ester, isopropylthiomethyl ester, etc.);
mono(or di or tri)-halo(lower)alkyl ester (e.g., 2-iodoethyl ester, 2,2,2-trichloroethyl ester, etc.);
lower alkanoyloxy(lower)alkyl ester (e.g., acetoxymethylester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);
lower alkanesulfonyl(lower)alkyl ester (e.g., mesylmethyl ester, 2-mesylethyl ester etc.);
ar(lower)alkyl ester, for example, phenyl(lower)alkyl ester optionally substituted by one or more suitable substituent(s) such as nitro, hydroxy, lower alkoxy or the like (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-di-t-butylbenzyl ester, etc.); aryl ester optionally substituted by one or more suitable substituent(s) such as substituted or unsubstituted phenyl ester optionally substituted by halogen, lower alkoxy or the like (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; lower alkylthioester (e.g. methylthioester, ethylthioester, etc.) and the like.

Preferred examples of "a protected carboxy group" for $R^3$ and $R_a^3$ is an esterified carboxy group, and more preferably nitrophenyl(lower)alkyl ester (e.g. 4-nitrobenzyl ester, 4-nitrophenethyl ester, etc.) and the like.

Suitable "halogen" may include chlorine, bromine and iodine.

Suitable "an acid residue" may include lower alkanesulfonyloxy (e.g. mesyloxy, ethanesulfonyloxy, propanesulfonyloxy, 1-methylethanesulfonyloxy, butanesulfonyloxy, isobutanesulfonyloxy, pentanesulfonyloxy, hexanesulfonyloxy etc.), arenesulfonyloxy (e.g. benzenesulfonyloxy, p-toluenesulfonyloxy, etc.), halogen (e.g. chlorine, bromine, etc.) or the like.

Suitable "lower alkanesulfonyl" and "arenesulfonyl" may be the same as those moiety of "lower alkanesulfonyloxy" and "arenesulfonyloxy" in the explanation of the term "an acid residue" as aforementioned.

Suitable "salt" of the compounds (I-a) to (I-j), (II), (II$_a$), (II$_c$) to (II$_e$) and (III) may include the ones as illustrated for the compound (I).

The processes for the preparation of the object compound (I) of the present invention are explained in detail in the following.

(1) Process 1

The object compound (I-a) or a salt thereof can be prepared by reacting the compound (II) or a salt thereof with the compound (III) of the formula: $R^2$-O-P(OR$_a^2$)$_2$, wherein $R^2$ and $R_a^2$ are each as defined above or a salt thereof.

As to the starting compound (III), the compound, wherein $R^2$ is hydrogen, can also be represented by the phosphonate of the formula:

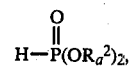

and accordingly such compound is included within the scope of the present process.

This reaction is usually carried out in a conventional solvent which does not adversely influence the reaction such as benzene, toluene, xylene, N,N-dimethylformamide, dimethylsulfoxide or a mixture thereof.

The reaction temperature is not critical and the reaction is preferably carried out from at ambient temperature to under heating.

When the compound (III), wherein $R^2$ is hydrogen, is used in this reaction, the reaction is preferably carried out in the presence of an organic or inorganic base such as alkali metal (e.g. lithium, sodium, potassium, etc.), alkaline earth metal (e.g. calcium, magnesium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), trialkylamine (e.g. triethylamine, etc.), pyridine compound (e.g. pyridine, lutidine, picoline, etc.), diazabicyclo compound (e.g. 1,5-diazabicyclo[4,3,0]-non-5-ene, 1,5-diazabicyclo[5,4,0]undec-5-ene, quaternary ammonium salt (e.g. triton B, etc.).

(2) Process 2

The object compound (I-b) or a salt thereof can be prepared by oxidizing the compound (I-a) or a salt thereof.

According to this process, the double bond in the starting compound (I-a) is changed from the 2nd position thereof to the 3rd position in the object compound (I-b).

The oxidizing agent to be used in this reaction may include an inorganic peracid or a salt thereof (e.g. periodic acid, persulfuric acid, or sodium or potassium salt thereof, etc.), an organic peracid or a salt thereof (e.g. perbenzoic acid, m-chloroperbenzoic acid, performic acid, peracetic acid, chloroperacetic acid, trifluoroperacetic acid, or sodium or potassium salt thereof, etc.), ozone, hydrogen peroxide, urea-hydrogen peroxide, or any other conventional oxidizing agent which can oxidize a thio group to a sulfinyl group.

The present reaction can also be carried out in the presence of a compound comprising Group Vb or VI b metal in the Periodic Table of elements, for example, tungstic acid, molybdic acid, vanadic acid, etc., or an alkali or an alkaline earth metal salt thereof.

The present oxidation reaction is usually carried out in a conventional solvent which does not adversely influence the reaction such as water, acetic acid, chloroform, methylene chloride, acetone, methanol, ethanol or a mixture thereof.

The reaction temperature is not critical and the reaction is preferably carried out from under cooling to at ambient temperature.

(3) Process 3

The object compound (I-c) or a salt thereof can be prepared by reducing the compound (I-b) or a salt thereof.

The reducing agent to be used in this reaction may include stannous halide (e.g. stannous chloride, etc.); metal thiosulfate (e.g. sodium thiosulfate, potassium thiosulfate, etc.) or said compound with acid halide (e.g. acetyl chloride, etc.); phosphorus halide (e.g. phosphorus trichloride, phosphorus pentachloride, etc.); silicon halide (e.g. silicon trichloride, etc.); or any other conventional reducing agent which can reduce a sulfinyl group to a thio group.

The present reduction reaction is usually carried out in a conventional solvent which does not adversely influence the reaction such as methylene chloride, tetrahydrofuran, benzene, toluene or a mixture thereof.

The reaction temperature is not critical and the reaction is preferably carried out from under cooling to at ambient temperature.

(4) Process 4

The object compound (I-e) or a salt thereof can be prepared by subjecting the compound (I-d) or a salt thereof to removal reaction of the amino-protective group.

Suitable method for this removal reaction includes hydrolysis, reduction, a combined method comprising iminohalogenation and iminoetherification, followed by hydrolysis, and the like.

In the above methods, suitable reagents to be used are exemplified as follows.

(i) For hydrolysis which refers to the same meaning as solvolysis including, for example, acidolysis, alcoholysis, aminolysis, hydrazinolysis, etc.:

Hydrolysis is preferably carried out in the presence of an acid or base.

Suitable acid is an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), an acidic ion-exchange resin and the like.

Suitable base is an inorganic base such as alkali or alkaline earth metal hydroxide, carbonate or bicarbonate (e.g. sodium hydroxide, potassium carbonate, sodium bicarbonate, calcium hydroxide, magnesium hydroxide, etc.), ammonium hydroxide and the like; an organic base such as an alkoxide or phenoxide of the above metal, (e.g. sodium ethoxide, sodium methoxide, lithium phenoxide), an amine such as mono-, di- or trialkylamine (e.g. methylamine, ethylamine, propylamine, isopropylamine, butylamine, N,N-dimethyl-1,3-propanediamine, trimethylamine, triethylamine, etc.), unsubstituted, mono- or disubstituted arylamine (e.g. aniline, N-methylaniline N,N-dimethylaniline, etc.) or a heterocyclic base (e.g. pyrrolidine, morpholine, N-methylmorpholine, N-methylpiperidine, N,N-dimethylpiperazine, pyridine, etc.), hydrazines (e.g. hydrazine, methylhydrazine, ethylhydrazine, etc.), a basic ion exchange resin and the like.

The hydrolysis is usually carried out in a conventional solvent which does not adversely influence the reaction such as water, methanol, ethanol, propanol, tetrahydrofuran, N,N-dimethylformamide, dioxane or a mixture thereof.

The reaction temperature of this hydrolysis is not critical and the reaction is usually carried out from under cooling to at ambient temperature.

(ii) For reduction:

Reduction is carried out in a conventional manner, including chemical reduction and catalytic reduction.

Suitable reducing agents to be used in chemical reduction are a metal (e.g. tin, zinc, iron, etc.), or a combination of metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction is usually carried out in a conventional solvent which does not adversely influence the reaction such as water, methanol, ethanol, propanol or a mixture thereof. Additionally, in case that the abovementioned acids to be used in chemical reduction are in liquid, they can also be used as a solvent. Further, a suitable solvent to be used in catalytic reduction may be the above-mentioned solvent, and other conventional solvent, such as diethyl ether, dioxane, tetrahydrofuran, etc., or a mixture thereof.

The reaction temperature of this reduction is not critical and the reaction is usually carried out from under cooling to at ambient temperature.

(iii) For combined method

In this process, when the protected amino group for $R_a^1$ is an organic carboxamide, the carboxamide bond can be more preferably cleaved by the following modified hydrolysis. That is, the compound (I-d) is first subjected to iminohalogenation, iminoetherification, and then hydrolysis. The first and second steps of this method are preferably carried out in an anhydrous solvent. Suitable solvent for the first step (i.e. iminohalogenation) is an aprotic solvent such as methylene chloride, chloroform, diethyl ether, tetrahydrofuran, dioxane, etc., and for the second step (i.e. iminoetherification) is usually the same as those in the above first step. These two steps and the last step (i.e. hydrolysis step) are most preferably conducted in one-batch system.

Suitable iminohalogenating agent includes a halogenating agent such as phosphorus compound (e.g. phosphorus trichloride, phosphorus pentachloride, phosphorus tribromide, phosphorus pentabromide, phosphorus oxychloride, etc.), thionyl chloride, phosgene, and the like.

Suitable iminoetherifying agent may be an alcohol such as an alkanol (e.g. methanol, ethanol, propanol, isopropanol, butanol, tert-butanol, etc.) or the corresponding alkanol having alkoxy (e.g. 2-methoxyethanol, 2-ethoxyethanol, etc.), and alkoxide of metal such as alkali metal, alkaline earth metal (e.g. sodium methoxide, potassium ethoxide, magnesium ethoxide, lithium methoxide, etc.), and the like. Thus obtained reaction product is, if necessary, hydrolyzed in a conventional manner. The hydrolysis is preferably carried out at ambient temperature or under cooling, and proceeds simply pouring the reaction mixture into water or a hydrophilic solvent such as alcohol (e.g. methanol, ethanol, etc.) moistened or admixed with water, and if necessary, with addition of an acid or base as exemplified in the hydrolysis.

(5) Process 5

The object compound (I-f) or a salt thereof can be prepared by reacting the compound (I-e) or a salt thereof with an acylating agent.

In this reaction, the starting compound (I-e) can be used in the activated form at the amino group of the 7th position thereof and such activated form may include a conventional one, for example, a silyl derivative formed by the reaction of the compound (I-e) with a silyl compound such as bis(trimethylsilyl)-acetamide, trimethylsilylacetamide, etc.; isocyanate, isothiocyanate, etc.; Schiff's base or its tautomeric enamine type isomer formed by the reaction of the amino group with a carbonyl compound such as an aldehyde compound (e.g., acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc.) or a ketone compound (e.g., acetone, methyl ethyl ketone, methyl isobutyl ketone, acetylacetone, ethyl acetoacetate, etc.), and the like.

The acylating agent to be used in this reaction may include an organic carboxylic and sulfonic acid or a reactive derivative thereof.

Suitable reactive derivative of the acylating agent may include, for example, an acid halide, an acid anhydride, an activated amide, an activated ester, and the like, and preferably an acid chloride and acid bromide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g., methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g., benzoic acid, etc.); a symmetrical acid anhydride; an activated acid amide with a heterocyclic compound containing imino function such as imidazole, 4-substituted imidazole, dimethylpyrazole, triazole or tetrazole; an activated ester (e.g., cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like. The suitable reactive derivative can optionally be selected from the above according to the kind of the compound (I-e) to be used practically.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, etc., or a mixture thereof.

Among these solvents, hydrophilic solvents may be used in a mixture with water. The reaction can usually be carried out from under cooling to at somewhat elevated temperature.

When the acylating agent is used in a form of the free acid or a salt in this reaction, the reaction is preferably carried out in the presence of a condensing agent such as a carbodiimide compound [e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g., N,N'-carbonylbis(2-methylimidazole), pentamethyleneketene-N-cyclohexylimine, diphenylketene-N-cyclohexylamine, etc.); an olefinic or acetylenic ether compounds (e.g., ethoxyacetylene, $\beta$-chlorovinylethyl ether), a sulfonic acid ester of N-hydroxybenzotriazole derivative [e.g., 1-(4-chlorobenzenesulfonyloxy)-6-chloro-1H-benzotriazole, etc.], a phosphorus compound (e.g., trialkyl phosphite, ethyl polyphosphate, isopropyl polyphosphate, phosphoryl chloride, phosphorus trichloride, triphenylphosphine, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as dimethylformamide, diethylacetamide, N-methylformamide or the like with a halogen compound such as thionyl chloride, phosphoryl chloride, phosgene or the like.

(6) Process 6:

The object compound (I-h) or a salt thereof can be prepared by subjecting the compound (I-g) or a salt thereof to removal reaction of the carboxy-protective group.

The reaction is carried out by a conventional method such as hydrolysis, reduction or the like.

The methods of hydrolysis and reduction, and the reaction conditions (e.g. reaction temperature, solvent, etc.) are substantially the same as those illustrated for the removal reaction of the amino-protective group for $R_a^1$ of the compound (I-d) in the Process 4, and therefore are to be referred to said explanation.

(7) Process 7:

The object compound (I-j) or a salt thereof can be prepared by subjecting the compound (I-i) or a salt thereof to removal reaction of the phosphono-protective group.

This reaction is carried out by a conventional method such as hydrolysis or the like.

The method of hydrolysis and the reaction conditions (e.g. reaction temperature, solvent, etc.) are substantially the same as those illustrated for the removal reaction of the amino-protective group for $R_a^1$ of the compound (I-d) in the Process 4, and therefore are to be referred to said explanation.

Preparations A to C for the preparation of the starting compounds (II-c) to (II-e) are explained in detail as follows.

(A) Preparation A

The compound (II-c) or a salt thereof can be prepared by reacting the compound (II-a) or a salt thereof with the compound (II-b) of the formula: $R^4$-Y, wherein $R^4$ and Y are each as defined above.

As to the starting compound (II-a) to be used in this preparation, it has been publicly known and can be prepared by the method known to the art in the cephalosporine field.

The present reaction is usually carried out in the presence of a base as aforementioned in the hydrolysis of the Process 4.

The present reaction is usually carried out in a conventional solvent which does not adversely influence the reaction such as tetrahydrofuran, N,N-dimethylformamide or the like, or a mixture thereof.

The reaction temperature is not critical and the reaction is usually carried out from under cooling to at ambient temperature.

(B) Preparation B

The object compound (II-d) or a salt thereof can be prepared by subjecting the compound (II-c) or a salt thereof to removal reaction of the amino-protective group.

The present reaction is substantially the same as the Process 4, and therefore the reaction conditions (e.g. an acid, base, reaction temperature, solvent, etc.) can be referred to those of the Process 4.

(C) Preparation C

The object compound (II-e) or a salt thereof can be prepared by reacting the compound (II-d) or a salt thereof with an acylating agent.

The acylating agent to be used in this reaction is the same as those explained in the Process 5.

Further, the present reaction is substantially the same as the Process 5, and therefore the reaction conditions (e.g. reaction temperature, solvent, etc.) can be referred to those of the Process 5.

It is to be noted that, in the aforementioned reactions including the Processes 1 to 7 and Preparations A to C and/or the post-treatment of the reaction mixture, in case that the compound possesses optical and/or geometrical isomer, it may occasionally be transformed into the other optical and/or geometrical isomer and such case is also included within the scope of the present invention.

In case that the object compound (I) have a free carboxy group at the 4th position thereof and/or a free amino group at the 7th position thereof, it may be transformed into its pharmaceutically acceptable salts by a conventional method.

The object compound (I) and pharmaceutically acceptable salts thereof of the present invention are novel and exhibit high antimicrobial activity, inhibiting the growth of a wide variety of pathogenic microorganisms including Gram-positive and Gram-negative microorganism and are useful as anti-microbial agents. Now, in order to show the utility of the object compound (I), the test data on the vitro antimicrobial activity of some representative compound (I) of this invention are shown in the following.

In vitro antimicrobial activity

Test Method

In vitro antimicrobial activity was determined by the two-fold agar-plate dilution method as described below.

One loopful of an overnight culture of each test strain in Trypticase-soy broth (approximately $10^6$ viable cells per ml.) was streaked on heart infusion agar (HI-agar) containing graded concentrations of antibiotics, and the minimal inhibitory concentration (MIC) was expressed in terms of $\mu g/ml$ after incubation at 37° C. for 20 hours.

| | Test compounds |  |
|---|---|---|
| No. 1 | 7-[2-(2-Aminothiazol-4-yl)-2-methoxyiminoacetamido]-3-phosphono-3-cephem-4-carboxylic acid (syn isomer). | |
| No. 2 | 7-[2-(2-Furyl)-2-methoxyiminoacetamido]-3-O,O-diethylphosphono-3-cephem-4-carboxylic acid (syn isomer). | |

| | Compounds | |
|---|---|---|
| Microorganisms | Compound 1 ($\mu g/ml$) | Compound 2 ($\mu g/ml$) |
| Bacillus subtilis ATCC 6633 | 50 | 3.13 |
| Proteus vulgaris IAM-1025 | 1.56 | 50 |

For therapeutic administration, the object compound (I) and pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age, conditions of the patient, a kind of disease, a kind of the compound (I) to be applied, etc. In general, amounts between 1 mg. and about 4000 mg. or even more per day may be administered to a patient. An average single dose of about 50 mg., 100 mg., 250 mg., 500 mg., 1000 mg., 2000 mg. of the object compound (I) of the present invention may be used in treating diseases infected by pathogenic microorganisms.

The following examples are given for the purpose of illustrating the present invention:

PREPARATION OF THE OBJECT COMPOUND

EXAMPLE 1

To a solution of 4-nitrobenzyl 7-[2-(2-formamidothiazol-4-yl)-2-methoxyiminoacetamido]-3-mesyloxy-3-cephem-4-carboxylate (syn isomer) (2.5 g.) in N,N-dimethylformamide (8 ml.) was added triethyl phosphite (2 g.), and the mixture was heated at 120° to 130° C. for 2 hours. After cooling, the reaction mixture was poured into a mixture of water (50 ml.) and ethyl acetate (50 ml.), and thereto was added 30% aqueous solution of hydrogen peroxide (2.3 ml.) in order to decompose the excess of triethyl phosphite. The ethyl acetate layer was separated out, washed with water (30 ml.×3) and an aqueous solution of sodium chloride, and then dried over anhydrous magnesium sulfate, followed by concentration of the solution under reduced pressure to give 4-nitrobenzyl 7-[2-(2-formamidothiazol-4-yl)-2-methoxyiminoacetamido]-3-O,O-diethylphosphono-2-cephem-4-carboxylate (syn isomer) (3.8 g.).

I.R. (Nujol): 3350, 1780, 1745, 1680, 1240 cm$^{-1}$

N.M.R. δppm (DMSO-d$_6$): 1.43 (6H, m), 3.93 (3H, s), 4.00 (4H, m), 5.07 (1H, d, J=8 Hz), 5.33 (1H, d, J=5 Hz), 5.40 (2H, s), 5.73 (1H, dd, J=5,8 Hz), 7.52 (1H, s), 7.57 (1H, d, J=8 Hz), 7.75 (2H, d, J=8 Hz), 8.33 (2H, d, J=8 Hz), 8.57 (1H, s), 9.77 (1H, d, J=8 Hz), 12.63 (1H, m)

EXAMPLE 2

To a solution of 4-nitrobenzyl 7-(2-phenylacetamido)-3-mesyloxy-3-cephem-4-carboxylate (6.8 g.) in N,N-dimethylformamide (10 ml.) was added triethyl phosphite (6.2 g.), and the mixture was heated at 120° to 130° C. for an hour. After cooling, the reaction mixture was poured into a mixture of water (150 ml.) and ethyl acetate (200 ml.) and thereto was added 30% aqueous solution of hydrogen peroxide (7 ml.) in order to decompose the excess of triethyl phosphite. The ethyl acetate layer was separated out, washed with an aqueous solution of sodium chloride and then dried over anhydrous magnesium sulfate, followed by concentration of the solution under reduced pressure. The residue was pulverized with diisopropyl ether to give 4-nitrobenzyl 7-(2-phenylacetamido)-3-O,O-diethylphosphono-2-cephem-4-carboxylate (6.2 g.).

I.R. (Nujol): 1780, 1740, 1670, 1240 cm$^{-1}$

N.M.R. δppm (DMSO-d$_6$): 1.13 (6H, m), 3.70 (2H, m), 3.97 (4H, m), 5.03 (1H, d, J=8 Hz), 5.27 (1H, d, J=5 Hz), 5.33 (2H, s), 5.40 (1H, m), 7.30 (5H, s), 7.40 (1H, d, J=8 Hz), 7.67 (2H, d, J=8 Hz), 8.27 (2H, d, J=8 Hz), 9.20 (1H, d, J=8 Hz)

EXAMPLE 3

To a suspension of 50% sodium hydride (0.26 g.) in N,N-dimethylformamide (3 ml.) was added dropwise diethyl phosphite (0.7 g.) under ice-cooling with stirring, and the stirring was continued at the same temperature for an hour. To the mixture was added dropwise a solution of 4-nitrobenzyl 7-(2-phenylacetamido)-3-mesyloxy-3-cephem-4-carboxylate (2.0 g.) in N,N-dimethylformamide (10 ml.) under ice-cooling with stirring and the stirring was continued at the same temperature for 1.5 hours. After ethyl acetate (30 ml.) was added to the reaction mixture, it was poured into water (50 ml.). The ethyl acetate layer was separated out, washed with an aqueous solution of sodium chloride and then dried over anhydrous magnesium sulfate, followed by concentration of the solution under reduced pressure. The residue was subjected to column chromatography on silica gel and elution was carried out with a mixture of benzene and ethyl acetate (3:1 by volume). Fractions containing a desired compound were collected and evaporated to dryness to give 4-nitrobenzyl 7-(2-phenylacetamido)-3-O,O-diethylphosphono-2-cephem-4-carboxylate (0.25 g.).

I.R. (Nujol): 1780, 1740, 1670, 1240 cm$^{-1}$

EXAMPLE 4

To a solution of 4-nitrobenzyl 7-[2-(2-formamidothiazol-4-yl)-2-methoxyiminoacetamido]-3-O,O-diethylphosphono-2-cephem-4-carboxylate (syn isomer) (1.5 g.) in methylene chloride (15 ml.) was added dropwise a solution of 3-chloroperbenzoic acid (0.9 g.) in a mixture of methylene chloride (5 ml.) and acetone (3 ml.) at 5° C. with stirring, and the stirring was continued at the same temperature for 2 hours. After the reaction mixture was adjusted to pH 7.5 with an aqueous solution of sodium bicarbonate, the organic layer was separated out, followed by washing with an aqueous solution of sodium chloride, drying over anhydrous magnesium sulfate and then concentrating under reduced pressure. The residue was pulverized with diisopropyl ether to give 4-nitrobenzyl 7-[2-(2-formamidothiazol-4-yl)-2-methoxyiminoacetamido]-3-O,O-diethylphosphono-3-cephem-4-carboxylate-1-oxide (syn isomer) (1.45 g.).

I.R. (Nujol): 3150, 1790, 1670, 1640, 1250 cm$^{-1}$

N.M.R. δppm (DMSO-d$_6$): 1.25 (6H, m), 3.70 (2H, m), 3.95 (3H, s), 4.06 (2H, m), 5.13 (1H, d, J=5 Hz), 5.47 (2H, m), 6.13 (1H, dd, J=5,8 Hz), 7.53 (1H, s), 7.78 (2H, d, J=8 Hz), 8.30 (2H, d, J=8 Hz), 8.57 (1H, s), 9.42 (1H, d, J=8 Hz), 12.60 (1H, m)

EXAMPLE 5

To a solution of 4-nitrobenzyl 7-(2-phenylacetamido)-3-O,O-diethylphosphono-2-cephem-4-carboxylate (28.2 g.) in methylene chloride (70 ml.) was added dropwise a solution of 3-chloroperbenzoic acid (14.8 g) in a mixture of methylene chloride (20 ml.) and acetone (20 ml.) under ice-cooling with stirring, and the stirring was continued at the same temperature for an hour. After the reaction mixture was poured into a mixture of water (300 ml.) and methylene chloride (100 ml.), it was adjusted to pH 7.5 with an aqueous solution of sodium bicarbonate. The organic layer was separated out, washed with an aqueous solution of sodium chloride, dried over anhydrous magnesium sulfate and then treated with an activated charcoal, followed by evaporating the filtrate to dryness under reduced pressure to give 4-nitrobenzyl 7-(2-phenylacetamido)-3-O,O-diethylphosphono-3-cephem-4-carboxylate-1-oxide (27.5 g.).

I.R. (Nujol): 1790, 1735, 1670, 1240 cm$^{-1}$

N.M.R. δppm (DMSO-d$_6$): 1.20 (6H, m), 3.57 (2H, m), 3.96 (4H, m), 4.97 (1H, d, J=5 Hz), 5.42 (2H, m), 5.96 (1H, dd, J=5,8 Hz), 7.28 (5H, s), 7.73 (2H, d, J=8 Hz), 8.25 (2H, d, J=8 Hz), 8.70 (1H, d, J=8 Hz)

EXAMPLE 6

To a solution of 4-nitrobenzyl 7-[2-(2-formamidothiazol-4-yl)-2-methoxyiminoacetamido]-3-O,O-diethylphosphono-3-cephem-4-carboxylate-1-oxide (syn isomer) (5.8 g.) in tetrahydrofuran (50 ml.) was added phosphorus trichloride (2.84 g.) at 5° C., and the mixture was stirred at ambient temperature for an hour. After ethyl acetate (200 ml.) was added thereto, it was poured into ice-water, followed by adjusting the resultant mixture to pH 7.0 with an aqueous solution of sodium bicarbonate. The organic layer was separated out, washed with an aqueous solution of sodium chloride and then dried over anhydrous magnesium sulfate, followed by concentration in vacuo. The residue obtained was pulverized with diisopropyl ether to give 4-nitrobenzyl 7-[2-(2-formamidothiazol-4-yl)-2-methoxyiminoacetamido]-3-O,O-diethylphosphono-3-cephem-4-carboxylate (syn isomer) (4.5 g.).

I.R. (Nujol): 3170, 1790, 1740, 1680, 1220 cm$^{-1}$

N.M.R. $\delta$ppm (DMSO-d$_6$): 1.21 (6H, m), 3.63 (2H, m), 3.97 (4H, m), 4.03 (3H, s), 5.40 (3 H, m), 5.92 (1H, m), 7.30 (1H, s), 7.75 (2H, d, J=8 Hz), 8.25 (2H, d, J=8 Hz), 8.50 (1H, s), 9.63 (1H, d, J=8 Hz), 12.58 (1H, m)

EXAMPLE 7

To a solution of 4-nitrobenzyl 7-(2-phenylacetamido)-3-O,O-diethylphosphono-3-cephem-4-carboxylate-1-oxide (7.2 g.) in tetrahydrofuran (70 ml.) was added at a time phosphorus trichloride (1.7 g.) and the mixture was stirred at ambient temperature for 3 hours. After the reaction mixture was poured into a mixture of water (400 ml.) and ethyl acetate (300 ml.), the organic layer was separated out, washed with an aqueous solution of sodium chloride and then dried over anhydrous magnesium sulfate, followed by concentration under reduced pressure. The residue obtained was pulverized with diisopropyl ether and collected by filtration to give 4-nitrobenzyl 7-(2-phenylacetamido)-3-O,O-diethylphosphono-3-cephem-4-carboxylate (7.0 g.).

I.R. (Nujol): 1790, 1740, 1660, 1230 cm$^{-1}$

N.M.R. $\delta$ppm (DMSO-d$_6$): 1.17 (6H, m), 3.47 (2H, s), 3.93 (4H, m), 5.20 (1H, d, J=5 Hz), 5.33 (2H, m), 5.80 (1H, dd, J=5,8 Hz), 7.20 (5H, s), 7.67 (2H, d, J=8 Hz), 8.20 (2H, d, J=8 Hz), 9.75 (1H, d, J=8 Hz)

EXAMPLE 8

To a suspension of phosphorus pentachloride (3.06 g.) in methylene chloride (30 ml.) was added pyridine (1.2 g.) and the mixture was stirred at ambient temperature for an hour. To this mixture was added at a time 4-nitrobenzyl 7-(2-phenylacetamido)-3-O,O-diethylphosphono-2-cephem-4-carboxylate (2.9 g.) at $-10°$ C., followed by stirring the mixture below 3° C. for 2 hours. After adding 2-methoxyethanol (1.7 g.) at $-20°$ C., the mixture was stirred at 5° C. for 2 hours. After the reaction mixture was poured into ice-water (100 ml.), the organic layer was separated out and extracted with water. The remained aqueous solution and this extract were combined, and thereto was added ethyl acetate (100 ml.), followed by adjusting to pH 7.5 with an aqueous solution of sodium carbonate. The ethyl acetate layer was separated out, washed with an aqueous solution of sodium chloride, dried over anhydrous magnesium sulfate, and then concentrated under reduced pressure to give 4-nitrobenzyl 7-amino-3-O,O-diethylphosphono-2-cephem-4-carboxylate (0.9 g.).

I.R. (Nujol): 3300, 1780, 1730, 1240 cm$^{-1}$

N.M.R. $\delta$ppm (DMSO-d$_6$): 1.25 (6H, m), 3.67 (4H, m), 4.92 (1H, d, J=9 Hz), 5.10 (1H, d, J=5 Hz), 5.42 (3H, m), 7.58 (1H, d, J=8 Hz), 7.75 (2H, d, J=8 Hz), 8.32 (2H, d, J=8 Hz)

EXAMPLE 9

To a suspension of phosphorus pentachloride (12.5 g.) in methylene chloride (70 ml.) was added dropwise pyridine (4.8 g.) at 5° C. and the mixture was stirred at ambient temperature for half the hour. To this solution was added at a time 4-nitrobenzyl 7-(2-phenylacetamido)-3-O,O-diethylphosphono-3-cephem-4-carboxylate (11.6 g.) at 5° C., followed by stirring the mixture at the same temperature for an hour. After adding 2-methoxyethanol (10 ml.) at $-20°$ C., the mixture was stirred at $-15°$ to $-5°$ C. for half an hour. After water (20 ml.) was added thereto, this mixture was poured into water (200 ml.), followed by adjusting to pH 6.0 with 20% aqueous solution of sodium hydroxide. The organic layer was separated out, washed with an aqueous solution of sodium chloride, dried over anhydrous magnesium sulfate, and then evaporated to dryness under reduced pressure to give 4-nitrobenzyl 7-amino-3-O,O-diethylphosphono-3-cephem-4-carboxylate (4.4 g.).

I.R. (Nujol): 3300, 1780, 1730, 1230 cm$^{-1}$

N.M.R. $\delta$ppm (DMSO-d$_6$): 1.17 (6H, m), 3.45 (2H, m), 3.92 (4H, m), 5.27 (2H, m), 5.33 (2H, m), 7.73 (2H, d, J=8 Hz), 8.25 (2H, d, J=8 Hz)

EXAMPLE 10

To a suspension of 2-(2-aminothiazol-4-yl)-2-methoxyiminoacetic acid (syn isomer) (1.2 g.) in tetrahydrofuran (10 ml.) was added dropwise phosphorus oxychloride (1.1 g.) below 8° C., and the mixture was stirred at the same temperature for 15 minutes. Thereto were added trimethylsilyl acetamide (1.1 g.), phosphorus oxychloride (1.1 g.) and N,N-dimethylformamide (0.58 g.) in turn under ice-cooling, whereafter the mixture was stirred for 20 minutes to prepare the activated acid solution.

On the other hand, to a solution of 4-nitrobenzyl 7-amino-3-O,O-diethylphosphono-3-cephem-4-carboxylate (2.7 g.) in a mixture of tetrahydrofuran (10 ml.) and ethyl acetate (10 ml.) was added trimethylsilyl acetamide (5.5 g.), and thereto was added at a time the activated acid solution prepared above at $-20°$ C., and the mixture was stirred at $-5°$ to 5° C. for half an hour. After adding water (20 ml.) and ethyl acetate (40 ml.) at $-20°$ C., the mixture was adjusted to pH 8.0 with an aqueous solution of sodium carbonate, followed by separating out the ethyl acetate layer. The remained aqueous solution was washed with ethyl acetate, and the washings and the ethyl acetate layer were combined, washed with an aqueous solution of sodium chloride, dried over anhydrous magnesium sulfate, and then treated with an activated charcoal. The filtrate was concentrated under reduced pressure and the residue was pulverized with diisopropyl ether to give 4-nitrobenzyl 7-[2-(2-aminothiazol-4-yl)-2-methoxyiminoacetamido]-3-O,O-diethylphosphono-3-cephem-4-carboxylate (syn isomer) (2.4 g.).

I.R. (Nujol): 3300, 3150, 1780, 1735, 1670, 1230 cm$^{-1}$

N.M.R. $\delta$ppm (DMSO-d$_6$): 1.17 (6H, m), 3.53 (2H, m), 3.80 (3H, s), 3.92 (4H, m), 5.30 (1H, d, J=5 Hz), 5.33 (2H, m), 5.90 (1H, dd, J=5,8 Hz), 6.70 (1H, s), 7.17 (2H, m), 7.70 (2H, d, J=8 Hz), 8.20 (2H, d, J=8 Hz), 9.67 (1H, d, J=8 Hz)

EXAMPLE 11

Tetrahydrofuran (3 ml.) was added to a Vilsmeier reagent, which was prepared by phosphorus oxychloride (0.22 g.) and N,N-dimethylformamide (0.11 g.) in a conventional manner, followed by adding at a time 2-(2-formamidothiazol-4-yl)-2-methoxyiminoacetic acid (syn isomer) (0.28 g.), and the mixture was stirred under ice-cooling for half an hour to prepare the activated acid solution. This solution was added at a time to a solution of 4-nitrobenzyl 7-amino-3-O,O-diethylphosphono-2-cephem-4-carboxylate (0.6 g.) and trimethylsilyl acetamide (1.4 g.) in tetrahydrofuran (10 ml.) at $-20°$ C., and the mixture was stirred at 0° C. for half an hour. After water (50 ml.) and ethyl acetate (50 ml.) were added thereto at $-20°$ C., it was adjusted to pH 7.5 with an aqueous solution of sodium carbonate. The ethyl acetate layer was separated out, washed with an aqueous solution of sodium chloride, dried over anhydrous magnesium sulfate and then concentrated under reduced pressure, followed by the residue was pulverized with diisopropyl ether to give 4-nitrobenzyl 7-[2-(2-formamidothiazol-4-yl)-2-methoxyiminoacetamido]-3-O,O-diethylphosphono-2-cephem-4-carboxylate (syn isomer) (0.7 g.).

I.R. (Nujol): 3350, 1780, 1745, 1680, 1240 cm$^{-1}$

EXAMPLE 12

4-Nitrobenzyl 7-amino-3-O,O-diethylphosphono-3-cephem-4-carboxylate (2.0 g.) was dissolved in tetrahydrofuran (10 ml.) and thereto was added water (10 ml.). To this solution was added dropwise a solution of 5-phenyl-1,3-dioxolane-2,4-dione (0.76 g.) in tetrahydrofuran (10 ml.) under ice-cooling with stirring, while the mixture was adjusted to pH 7.0 with an aqueous solution of sodium carbonate during the addition, and the stirring was continued at the same temperature for an hour. After addition of ethyl acetate (80 ml.), it was adjusted to pH 8.0 with an aqueous solution of sodium carbonate. The ethyl acetate layer was separated out, washed with an aqueous solution of sodium chloride, dried over anhydrous magnesium sulfate and then concentrated under reduced pressure, followed by the residue was pulverized with diisopropyl ether to give 4-nitrobenzyl 7-(2-phenylglycoloylamino)-3-O,O-diethylphosphono-3-cephem-4-carboxylate (2.0 g.).

I.R. (Nujol): 3300, 1785, 1740, 1660, 1220 cm$^{-1}$

N.M.R. δppm (DMSO-d$_6$): 1.17 (6H, m), 3.57 (2H, m), 3.93 (4H, m), 5.33 (3H, m), 5.83 (1H, m), 7.40 (5H, m), 7.75 (2H, d, J=8 Hz), 8.27 (2H, d, J=8 Hz), 9.00 (1H, d, J=8 Hz)

EXAMPLE 13

Tetrahydrofuran (10 ml.) was added to a Vilsmeier reagent, which was prepared by phosphorus oxychloride (0.69 g.) and N,N-dimethylformamide (0.32 g.) in a conventional manner, followed by adding 2-(2-furyl)-2-methoxyiminoacetic acid (syn isomer) (0.72 g.), and the mixture was stirred for half an hour to prepare the activated acid solution. This solution was added at a time to a solution of 4-nitrobenzyl 7-amino-3-O,O-diethylphosphono-3-cephem-4-carboxylate (2.0 g.) and trimethylsilyl acetamide (3.3 g.) in tetrahydrofuran (12.5 ml.) at −20° C., and the mixture was stirred at −10° to 0° C. for half an hour. After water (30 ml.) and ethyl acetate (80 ml.) were added to the reaction mixture at −20° C., it was adjusted to pH 8.0 with an aqueous solution of sodium carbonate. The ethyl acetate layer was separated out, washed with an aqueous solution of sodium chloride, dried over anhydrous magnesium sulfate and then evaporated to dryness under reduced pressure, followed by the residue was pulverized with diisopropyl ether to give 4-nitrobenzyl 7-[2-(2-furyl)-2-methoxyiminoacetamido]-3-O,O-diethylphosphono-3-cephem-4-carboxylate (2.5 g.).

I.R. (Nujol): 3350, 1790, 1740, 1675, 1230 cm$^{-1}$

N.M.R. δppm (DMSO-d$_6$): 1.25 (6H, m), 3.70 (2H, m), 3.92 (3H, s), 4.00 (4H, m), 5.37 (1H, d, J=5 Hz), 5.42 (2H, s), 6.00 (1H, dd, J=5,8 Hz), 6.68 (2H, s), 7.75 (2H, d, J=8 Hz), 7.80 (1H, s), 8.27 (2H, d, J=8 Hz), 9.92 (1H, d, J=8 Hz)

EXAMPLE 14

4-Nitrobenzyl 7-[2-(2-formamidothiazol-4-yl)-2-methoxyiminoacetamido]-3-O,O-diethylphosphono-3-cephem-4-carboxylate (syn isomer) (4.4 g.) was dissolved in a mixture of tetrahydrofuran (150 ml.) and acetic acid (1 ml.), and thereto was added a suspension of palladium on carbon (2.5 g.) in a mixture of water (5 ml.) and ethanol (10 ml.). The mixture was stirred at ambient temperature in hydrogen atmosphere for 5 hours. After the catalyst was removed by filtration, the filtrate was concentrated in vacuo to give a residue, to which were added water (100 ml.) and ethyl acetate (100 ml.), followed by adjusting to pH 7.5 with an aqueous solution of sodium carbonate. After the precipitates were removed by filtration, the aqueous layer was separated out from the filtrate, adjusted to pH 6.0 with diluted hydrochloric acid, and then washed with ethyl acetate. The aqueous solution was adjusted to pH 2.0 with diluted hydrochloric acid, and extracted with ethyl acetate, whereafter the extract was washed with an aqueous solution of sodium chloride and dried over anhydrous magnesium sulfate, followed by concentration under reduced pressure. The residue was pulverized with diisopropyl ether to give 7-[2-(2-formamidothiazol-4-yl)-2-methoxyiminoacetamido]-3-O,O-diethylphosphono-3-cephem-4-carboxylic acid (syn isomer) (0.3 g.).

I.R. (Nujol): 3300, 3250, 1800, 1740, 1690, 1240 cm$^{-1}$

N.M.R. δppm (DMSO-d$_6$): 1.24 (6H, m), 3.54 (2H, m), 3.95 (4H, m), 4.00 (3H, s), 5.25 (1H, d, J=5 Hz), 5.82 (1H, m), 7.28 (1H, s), 8.50 (1H, s), 9.60 (1H, d, J=8 Hz), 12.50 (1H, m)

EXAMPLE 15

4-Nitrobenzyl 7-[2-(2-furyl)-2-methoxyiminoacetamido]-3-O,O-diethylphosphono-3-cephem-4-carboxylate (syn isomer) (2.4 g.) was dissolved in tetrahydrofuran (50 ml.), and thereto was added acetic acid (0.5 ml.), followed by adding a suspension of palladium on carbon (1.0 g.) in a mixture of 50% aqueous ethanol (10 ml.). The mixture was stirred at ambient temperature in hydrogen atmosphere for 1.5 hours. After the catalyst was removed by filtration, the filtrate was concentrated under reduced pressure to give a residue, to which ethyl acetate (30 ml.) was added, followed by adjusting to pH 8.0 with an aqueous solution of sodium carbonate. The aqueous solution was separated out, adjusted to pH 6.5 with diluted hydrochloric acid and washed with ethyl acetate.

The aqueous solution was adjusted to pH 3.0 with diluted hydrochloric acid and then extracted with ethyl acetate, whereafter the extract was washed with an aqueous solution of sodium chloride and dried over anhydrous magnesium sulfate, followed by concentration under reduced pressure. The residue was pulverized with diisopropyl ether to give 7-[2-(2-furyl)-2-methoxyiminoacetamido]-3-O,O-diethylphosphono-3-cephem-4-carboxylic acid (syn isomer) (0.9 g.).

I.R. (Nujol): 3200, 1800, 1745, 1680, 1230 cm$^{-1}$

N.M.R. δppm (DMSO-d$_6$): 1.08 (6H, t, J=7 Hz), 3.63 (2H, m), 3.92 (3H, s), 4.10 (4H, q, J=7 Hz), 5.30 (1H, d, J=5 Hz), 5.92 (1H, dd, J=5,8 Hz), 6.67 (2H, s), 8.18 (1H, m), 9.87 (1H, d, J=8 Hz)

EXAMPLE 16

4-Nitrobenzyl 7-(2-phenylacetamido)-3-O,O-diethylphosphono-3-cephem-4-carboxylate (2.0 g.) was dissolved in a mixture of tetrahydrofuran (60 ml.) and acetic acid (0.3 ml.), and thereto was added a suspension of palladium on carbon (0.8 g.) in a mixture of water (3 ml.) and ethanol (5 ml.). The mixture was stirred at ambient temperature in hydrogen atmosphere for 2 hours. After the catalyst was removed by filtration, the filtrate was concentrated under reduced pressure to give a residue, to which ethyl acetate and water were added, followed by adjusting to pH 7.5 with an aqueous solution of sodium carbonate. After the precipitates were removed by filtration, the aqueous solution was separated out from the filtrate, adjusted to pH 6.0 with diluted hydrochloric acid and washed with ethyl acetate. The aqueous solution was further adjusted to pH 2.5 with diluted hydrochloric acid and extracted with ethyl acetate, whereafter the extract was washed with an aqueous solution of sodium chloride and dried over anhydrous magnesium sulfate, followed by concentration under reduced pressure.

The residue was pulverized with diisopropyl ether to give 7-(2-phenylacetamido)-3-O,O-diethylphosphono-3-cephem-4-carboxylic acid (0.8 g.).

I.R. (Nujol): 3300, 1800, 1745, 1670, 1610, 1230 cm$^{-1}$

N.M.R. $\delta$ppm (DMSO-d$_6$): 1.19 (6H, t, J=8 Hz), 3.44 (2H, m), 3.48 (2H, s), 3.94 (4H, m), 5.12 (1H, d, J=5 Hz), 5.71 (1H, dd, J=5,8 Hz), 7.21 (5H, s), 9.60 (1H, d, J=8 Hz)

EXAMPLE 17

4-Nitrobenzyl 7-[2-(2-aminothiazol-4-yl)-2-methoxyiminoacetamido]-3-O,O-diethylphosphono-3-cephem-4-carboxylate (syn isomer) (2.4 g.), was dissolved in a mixture of tetrahydrofuran (80 ml.) and acetic acid (0.5 ml.), and thereto was added a suspension of palladium on carbon (1.5 g.) in 50% aqueous ethanol (10 ml.). The mixture was stirred at ambient temperature in hydrogen atmosphere for 3 hours. After the catalyst was removed by filtration, the filtrate was concentrated under reduced pressure to give 7-[2-(2-aminothiazol-4-yl)-2-methoxyiminoacetamido-3-O,O-diethylphosphono-3-cephem-4-carboxylic acid] (syn isomer). To this product was added ethyl acetate, followed by adjusting to pH 8.0 with an aqueous solution of sodium carbonate. After the precipitates were removed by filtration, the resultant aqueous solution was adjusted to pH 6.5 with diluted hydrochloric acid, followed by removing the organic solvent in vacuo. The remaining aqueous solution was adjusted to pH 3.7 with diluted hydrochloric acid and passed through a column packed with a nonionic adsorption resin "Diaion HP-20" (manufactured by Mitsubishi Chemical Industries Ltd.). Elution was carried out with 20% aqueous acetone, and the fractions containing a desired compound were collected and evaporated to dryness. The residue obtained was lyophilized to give 7-[2-(2-aminothiazol-4-yl)-2-methoxyiminoacetamido]-3-phosphono-3-cephem-4-carboxylic acid (syn isomer) (0.5 g.).

I.R. (Nujol): 3250, 1770, 1660 cm$^{-1}$

N.M.R. $\delta$ppm (D$_2$O+N$_a$HCO$_3$): 3.61 (2H, m), 3.76 (3H, s), 5.18 (1H, d, J=5 Hz), 5.73 (1H, d, J=5 Hz), 6.95 (1H, s),

EXAMPLE 18

To a solution of 4-nitrobenzyl 7-amino-3-O,O-diethylphosphono-3-cephem-4-carboxylate (1.0 g) in tetrahydrofuran (15 ml) was added acetic anhydride with formic acid (0.84 g), and the mixture was stirred at 23° to 25° C. for 15 minutes. The reaction mixture was poured into a mixture of water (30 ml) and ethyl acetate (30 ml) under ice-cooling, and then adjusted to pH 7.0-7.5 with an aqueous solution of sodium bicarbonate, followed by stirring for an hour. The separated ethyl acetate layer was washed with an aqueous solution of sodium chloride, dried over anhydrous magnesium sulfate and then filtered, followed by evaporation under reduced pressure to give a residue (1.0 g), which was chromatographed on silica gel (12 ml) using a mixture of benzene and ethyl acetate (3:1 by volume) as an eluent. The fractions containing a desired compound were collected and then evaporated to give 4-nitrobenzyl 7-formamido-3-O,O-diethylphosphono-3-cephem-4-carboxylate (0.6 g.).

I.R. (Nujol): 3180, 1788, 1738, 1684, 1606, 1230 cm$^{-1}$

N.M.R. $\delta$ppm (DMSO-d$_6$): 1.0-1.5 (6H, m), 3.65 (2H, s) 3.7-4.2 (4H, m), 5.29 (1H, d, J=5 Hz) 5.39 (2H, broad s), 5.92 (1H, dd, J=5 Hz, 8 Hz), 7.73, 8.26 (4H, ABq, J=9 Hz), 8.16 (1H, s), 9.15 (1H, d, J=9 Hz)

EXAMPLE 19

A mixture of N,N-dimethylformamide (0.715 g) phosphorus oxychloride (0.341 g) in tetrahydrofuran (1 ml) was stirred at −10° to 0° C. for a while to prepare the solution of Vilsmeier reagent. To this solution were added tetrahydrofuran (10 ml) and 2-phenylpropanedioic acid monobenzyl ester (1.146 g) with stirring, and the stirring was continued at 0° C. for 40 minutes. The resultant solution was added dropwise to a solution of 4-nitrobenzyl 7-amino-3-O,O-diethylphosphono-3-cephem-4-carboxylate (2.0 g) in tetrahydrofuran (20 ml) and water (10 ml) at 5° C. with stirring, and the stirring was continued for half an hour. During the stirring, the reaction mixture was adjusted to pH 6.0 with an aqueous solution of sodium bicarbonate. After the reaction mixture was poured into ethyl acetate (100 ml), it was adjusted to pH 7.5 with an aqueous solution of sodium bicarbonate. The separated ethyl acetate layer was washed twice with an aqueous solution of sodium chloride, dried over anhydrous magnesium sulfate and then evaporated under reduced pressure to give a residue (2.56 g), which was chromatographed on silica gel (75 ml) using a mixture of benzene and ethyl acetate (3:1 by volume) as an eluent. The fractions containing a desired compound were collected and then evaporated to give 4-nitrobenzyl 7-(2-benzyloxycarbonyl-2-phenylacetamido)-3-O,O-diethylphosphono-3-cephem-4-carboxylate (0.68 g).

I.R. (Nujol): 3200, 1788, 1739, 1679, 1600, cm$^{-1}$

N.M.R. $\delta$ppm (DMSO-d$_6$): 1.2 (6H, m), 3.73 (2H, m), 4.0 (4H, m), 4.90 (1H, s), 5.20 (2H, broad s), 5.22 (1H, d, J=5 Hz), 5.40 (2H, broad s), 5.83 (1H, dd, J=5 Hz, 8 Hz), 7.37 (10H, s), 7.73, 8.25 (4H, ABq, J=9 Hz), 9.50 (1H, d, J=8 Hz)

PREPARATION OF THE STARTING COMPOUND

PREPARATION 1

4-Nitrobenzyl 7-(2-phenylacetamido)-3-hydroxy-3-cephem-4-carboxylate (100 g.) was dissolved in a mixture of N,N-dimethylformamide (0.4 l.) and tetrahydrofuran (0.4 l.), and thereto was added potassium carbonate (29 g.). To the mixture was added dropwise mesyl chloride (26.3 g.) at 5° C. with stirring, and the stirring was continued at the same temperature for 1.5 hours. After the reaction mixture was poured into a mixture of water (3 l.) and ethyl acetate (3 l.) the organic layer was separated out, washed with water (1 l.) and a saturated aqueous solution of sodium chloride (1 l.×2) and then dried over anhydrous magnesium sulfate, followed by treating with an activated charcoal. The filtrate was concentrated in vacuo, and the precipitated crystals were collected by filtration and washed with diisopropyl ether to give 4-nitrobenzyl 7-(2-phenylacetamido)-3-mesyloxy-3-cephem-4-carboxylate (81.8 g.).

I.R. (Nujol): 3280, 1790, 1780, 1710, 1650 cm$^{-1}$

N.M.R. δppm (DMSO-d$_6$): 3.40 (3H, s), 3.53 (2H, s), 3.87 (2H, AB$_q$, J=18 Hz), 5.23 (1H, d, J=5 Hz), 5.42 (2H, s), 5.82 (1H, dd, J=5,8 Hz), 7.32 (5H, s), 7.68 (2H, d, J=9 Hz), 8.25 (2H, d, J=9 Hz), 9.90 (1H, d, J=8 Hz)

PREPARATION 2

To a suspension of 4-nitrobenzyl 7-(2-phenylacetamido)-3-mesyloxy-3-cephem-4-carboxylate (11 g.) in methylene chloride (100 ml.) were added pyridine (2.37 g.) at ambient temperature and then phosphorus pentachloride (5.4 g.) at 0° C. with stirring, whereafter the mixture was stirred at −3° to 3° C. for 2 hours. After adding methanol (5.2 g.) at −20° C., the stirring was continued at the same temperature for additional an hour. The reaction mixture was poured into water and adjusted to pH 7.5 with sodium bicarbonate, followed by extraction with ethyl acetate (500 ml.). The extract was washed with an aqueous solution of sodium chloride, dried over anhydrous magnesium sulfate, and then concentrated under reduced pressure. The residue was pulverized with diethyl ether to give 4-nitrobenzyl 7-amino-3-mesyloxy-3-cephem-4-carboxylate (8.8 g.).

N.M.R. δppm (DMSO-d$_6$): 3.32 (2H, m), 3.42 (3H, s), 5.13 (1H, d, J=5 Hz), 5.40 (3H, m), 7.68 (2H, d, J=8 Hz), 8.20 (2H, d, J=8 Hz)

PREPARATION 3

To a mixture of N,N-dimethylformamide (1 g.) and tetrahydrofuran (1 ml.) was added phosphorus oxychloride (2 g.) under ice-cooling with stirring, and the stirring was continued below 5° C. for 40 minutes. After addition of tetrahydrofuran (20 ml.), 2-(2-formamidothiazol-4-yl)-2-methoxyiminoacetic acid (syn isomer) (2.3 g.) was added thereto under ice-cooling, followed by stirring for half an hour to give an activated acid solution.

On the other hand, to a suspension of 4-nitrobenzyl 7-amino-3-mesyloxy-3-cephem-4-carboxylate (4.3 g.) in tetrahydrofuran (40 ml.) was added trimethylsilylacetamide (9.2 g.) and cooled to −20° C. To this solution was added at a time the above-obtained activated acid solution, and the mixture was stirred at the same temperature for an hour. After water was added to the reaction mixture, it was adjusted to pH 7.5 with an aqueous solution of sodium bicarbonate, and then extracted with ethyl acetate. The remained aqueous solution was further extracted with ethyl acetate. After the combined extracts were washed with an aqueous solution of sodium chloride, dried over anhydrous magnesium sulfate and then treated with an activated charcoal, the filtrate was concentrated under reduced pressure. The residue was pulverized with diisopropyl ether to give 4-nitrobenzyl 7-[2-(2-formamidothiazol-4-yl)-2-methoxyiminoacetamido]-3-mesyloxy-3-cephem-4-carboxylate (syn isomer) (3.2 g.).

I.R. (Nujol): 3500, 1785, 1730, 1690, 1660 cm$^{-1}$

N.M.R. δppm (DMSO-d$_6$): 3.46 (3H, s), 3.94 (3H, s), 5.36 (1H, d, J=5 Hz), 5.44 (2H, s), 6.00 (1H, dd, J=5,8 Hz), 7.44 (1H, s), 7.70 (2H, d, J=8 Hz), 8.24 (2H, d, J=8 Hz), 8.54 (1H, s), 9.80 (1H, d, J=8 Hz), 12.60 (1H, s)

We claim:

1. A compound of the formula:

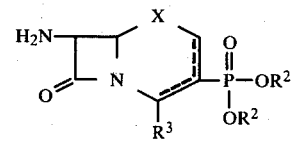

wherein $R^2$ is hydrogen or lower alkyl, $R^3$ is carboxy or a protected carboxy group, X is —S— or

and the dotted line bridging the 2 to 4-positions of the formula indicates that the compound may be the 2 or 3-cephem derivative, and pharmaceutically acceptable salts thereof.

2. The compound according to claim 1, wherein $R^2$ is hydrogen or lower alkyl, $R^3$ is carboxy or an esterified carboxy group and X is —S— or

3. The compound according to claim 1, wherein $R^2$ is hydrogen or lower alkyl, $R^3$ is carboxy or nitrophenyl(lower)alkoxycarbonyl and X is —S— or

4. The compound according to claim 1, wherein $R^3$ is carboxy and X is —S—.

5. The compound according to claim 1, wherein X is —S—.

* * * * *